US010041942B2

(12) United States Patent
Gunnerson et al.

(10) Patent No.: US 10,041,942 B2
(45) Date of Patent: Aug. 7, 2018

(54) ROTATABLE FLUID SAMPLE COLLECTION DEVICE

(71) Applicant: ORTHO-CLINICAL DIAGNOSTICS, INC., Raritan, NJ (US)

(72) Inventors: Kory A. Gunnerson, Cincinnati, OH (US); Raymond F. Jakubowicz, Rush, NY (US); Andrew M. Kirsch, Webster, NY (US); James Ellis Robinson, Rochester, NY (US); Daniel P. Salotto, Rochester, NY (US); David A. Tomasso, Rochester, NY (US); Zhong Ding, Pittsford, NY (US); William Franklin Gottermeier, Pittsford, NY (US); Aaron Michael Swick, Cincinnati, OH (US)

(73) Assignee: ORTHO-CLINICAL DIAGNOSTICS, INC., Raritan, NJ (US)

( * ) Notice: Subject to any disclaimer, the term of this patent is extended or adjusted under 35 U.S.C. 154(b) by 0 days.

(21) Appl. No.: 15/618,225

(22) Filed: Jun. 9, 2017

(65) Prior Publication Data

US 2017/0276673 A1    Sep. 28, 2017

Related U.S. Application Data

(62) Division of application No. 14/208,651, filed on Mar. 13, 2014, now Pat. No. 9,678,069.
(Continued)

(51) Int. Cl.
*G01N 33/53* (2006.01)
*G01N 33/558* (2006.01)
(Continued)

(52) U.S. Cl.
CPC .......... *G01N 33/558* (2013.01); *A61B 5/157* (2013.01); *A61B 5/150022* (2013.01);
(Continued)

(58) Field of Classification Search
None
See application file for complete search history.

(56) References Cited

U.S. PATENT DOCUMENTS 5,120,643 A    6/1992  Ching et al.
5,559,041 A    9/1996  Kang et al.
(Continued)

FOREIGN PATENT DOCUMENTS

EP    1 916 524 A1    4/2008
EP    2 096 444 A1    9/2009
(Continued)

*Primary Examiner* — Rebecca L Martinez
(74) *Attorney, Agent, or Firm* — K&L Gates LLP; Louis C. Cullman; Joseph Arand

(57) ABSTRACT

A sample collection device for a fluid sample includes: a body including a capillary channel having a first end and a second end, wherein the first end is adapted to draw the fluid into the channel by capillary action; an air vent located in the vicinity of the second end and in fluid communication with the capillary channel; a barrier positioned within the capillary channel to prevent flow of the fluid by capillary action thereacross; and features on opposing sides of the body to form an axis of rotation, which is substantially perpendicular to the overall direction of the capillary channel from the first end to the second end. In a preferred embodiment, the sample collection device is adapted to rotate about the axis of rotation within a cartridge having a sample manipulation device to bring the first end into position with the sample manipulation device.

20 Claims, 9 Drawing Sheets

Related U.S. Application Data

(60) Provisional application No. 61/791,334, filed on Mar. 15, 2013.

(51) Int. Cl.
| | | |
|---|---|---|
| *A61B 5/15* | (2006.01) | |
| *B01L 3/00* | (2006.01) | |
| *G01N 33/72* | (2006.01) | |
| *A61B 5/157* | (2006.01) | |
| *A61B 5/1455* | (2006.01) | |

(52) U.S. Cl.
CPC .. *A61B 5/150213* (2013.01); *A61B 5/150267* (2013.01); *A61B 5/150343* (2013.01); *A61B 5/150755* (2013.01); *B01L 3/50273* (2013.01); *G01N 33/726* (2013.01); *A61B 5/1455* (2013.01); *A61B 5/150809* (2013.01); *A61B 2562/0295* (2013.01); *G01N 33/5302* (2013.01); *Y10T 436/25375* (2015.01)

(56) References Cited

U.S. PATENT DOCUMENTS

| | | | |
|---|---|---|---|
| 5,714,389 A | 2/1998 | Carlton et al. | |
| 6,139,800 A | 10/2000 | Chandler | |
| 6,228,660 B1 | 5/2001 | May et al. | |
| 6,372,542 B1 | 4/2002 | Martin et al. | |
| 6,733,682 B1 | 5/2004 | Björkman et al. | |
| 6,811,736 B1 | 11/2004 | Ohman et al. | |
| 6,884,370 B2 | 4/2005 | Ohman et al. | |
| 7,416,700 B2 | 8/2008 | Buechler et al. | |
| 2003/0012694 A1* | 1/2003 | Roesicke | B01L 3/502 422/400 |
| 2005/0042766 A1 | 2/2005 | Ohman et al. | |
| 2006/0239859 A1 | 10/2006 | Ohman et al. | |
| 2006/0285996 A1 | 12/2006 | Ohman et al. | |
| 2006/0289787 A1 | 12/2006 | Ohman et al. | |
| 2007/0231883 A1 | 10/2007 | Lindstrom et al. | |
| 2013/0210036 A1 | 8/2013 | Kanaley et al. | |
| 2014/0206098 A1 | 7/2014 | Hosimer et al. | |

FOREIGN PATENT DOCUMENTS

| | | |
|---|---|---|
| WO | WO 03/103835 A1 | 12/2003 |
| WO | WO 2005/089082 A2 | 9/2005 |
| WO | WO 2005/118139 A1 | 12/2005 |
| WO | WO 2006/034104 A1 | 3/2006 |
| WO | WO 2006/137785 A1 | 12/2006 |
| WO | WO 2007/057704 A1 | 5/2007 |
| WO | WO 2007/149042 A1 | 12/2007 |
| WO | WO 2012/048388 A1 | 4/2012 |

* cited by examiner

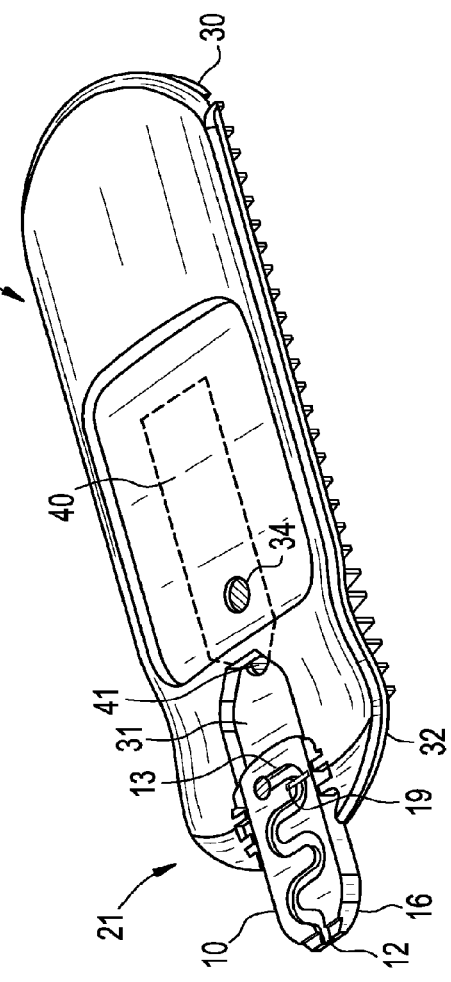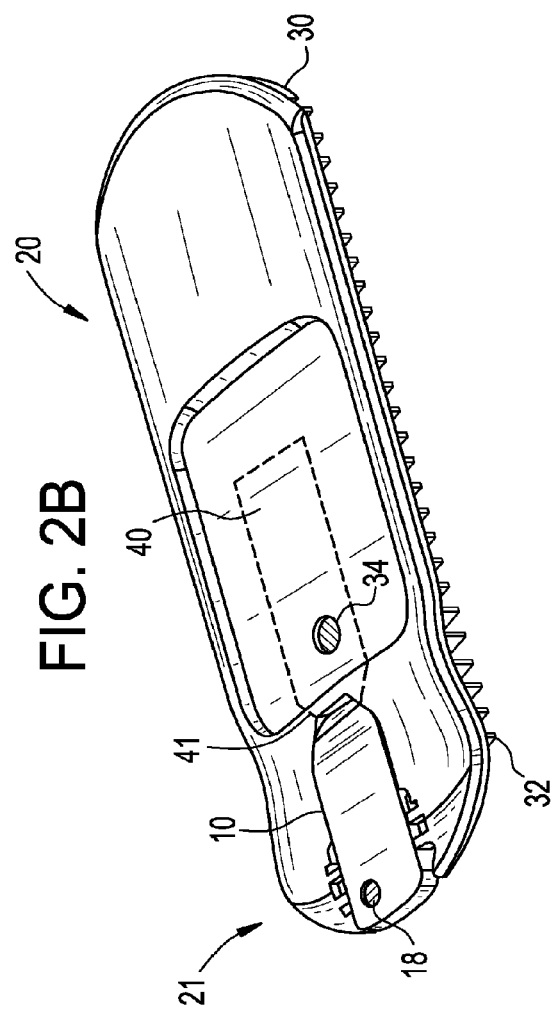

ROTATABLE FLUID SAMPLE COLLECTION DEVICE

CROSS REFERENCE TO RELATED APPLICATIONS

This patent application is a divisional application of U.S. patent application Ser. No. 14/208,651, filed Mar. 13, 2014, which claims priority upon U.S. Patent Application No. 61/791,334, filed Mar. 15, 2013, the entire contents of each application being incorporated herein by reference.

FIELD OF THE INVENTION

This present invention relates to a device for use in collecting and storing fluid samples, particularly biological samples, such as whole (unseparated) blood, serum, plasma and urine taken from the human or animal body. Such biological samples may be used in diagnostic and other biochemical tests. More particularly, the present invention relates to such a device which relies on capillary action for the collection of the fluid sample. The invention also relates to a working element comprising the fluid sample collection device. The present invention also relates to the field of diagnostic assays, and in particular to lateral flow assays where an analyte to be detected is present in a biological sample.

BACKGROUND

Fluid samples taken from the human or animal body are required for a wide variety of diagnostic and other biochemical tests, including the measurement of immunological reactions (immunoassays). There is accordingly a need for a device which can be conveniently used for collecting and storing such samples. Since the samples may pose a microbiological contamination or heath risk, the device used for their collection should not allow unintended release of the samples during storage, transportation or manipulation. The sample collection device is preferably disposable.

A known sample collection device for whole blood comprises an open-ended linear capillary tube formed of glass. The tube typically has an internal diameter of between one and two millimeters. To prevent clotting of the collected blood, the internal surface of the tube may be coated with a suitable anticoagulant such as heparin, which may also serve to reduce the contact angle between the sample and the side of the tube.

In use of the known device, the skin on the tip of a patient's finger is pierced by a lancet or other sharp piercing member. The blood so elicited is drawn into the linear tube by capillary action. The volume of the blood sample and the rate at which it is collected may be maximized by holding the tube with a generally horizontal orientation. The volume of the sample collected in this way is usually of the order of 25-100 µL.

A problem associated with the blood sample collection device described above relates to the transportation and handling of the sample subsequent to its collection. In particular, when the orientation of the linear tube is changed, there is a risk that gravitational forces acting on the sample may exceed the intermolecular forces which maintain the sample in the tube, leading to the unintended release of a portion of the sample and the associated microbiological contamination or heath risk. This problem may be exacerbated when the linear tube is also subjected to accelerations caused by sudden movements or decelerations caused by small knocks, etc.

To prevent the unintended release of the sample, it is known to stopper one or both ends of the linear capillary tube, for example using silicone bungs or sealant. However, there remains a risk that a portion of the sample may be accidentally released before the ends of the tube have been sealed or after the seal has been removed for subsequent processing.

There are many challenges in designing a sample collection device to be use in conjunction with further sample manipulation such as diagnostic testing. These include: minimizing contamination due to premature dispense or leakage from the sample collection device; enabling collection directly from a patient (i.e., finger stick) as well as from peripheral sample collection devices such as collection tubes or syringes; insufficient transfer of the sample to the manipulation device; ensuring collection volume is sufficient for the sample manipulation process; sample evaporation; minimizing the ability to re-open the sample collection device to avoid contamination; or other sources of inaccuracies in the sample manipulation process. Thus, there is a need in the art for an improved sample collection device for that overcomes the problems of the known art described above. In particular there is a need in the art for an improved sample collection device, which fluids are generally aqueous, and particularly such a device for which the risk of accidentally release of a portion of the sample subsequent to its collection may be reduced.

SUMMARY OF THE INVENTION

The present invention is directed to an assay device that alleviates one or more the foregoing problems described above.

One aspect of the invention is directed to a sample collection device for a fluid sample, the device comprising: a body including a capillary channel having a first end and a second end, wherein the first end is adapted to draw the fluid into the channel by capillary action; an air vent located in the vicinity of the second end and in fluid communication with the capillary channel; a barrier positioned within the capillary channel to prevent flow of the fluid by capillary action thereacross; and features on opposing sides of the body to form an axis of rotation, which is substantially perpendicular to the overall direction of the capillary channel from the first end to the second end. In a preferred embodiment, the sample collection device is adapted to rotate about the axis of rotation within a cartridge having a sample manipulation device to bring the first end into position with the sample manipulation device.

Another aspect of the invention is directed to a working element comprising: a sample collection device for a fluid sample, the device comprising: a body including a capillary channel having a first end and a second end, wherein the first end is adapted to draw the fluid into the channel by capillary action; an air vent located in the vicinity of the second end and in fluid communication with the capillary channel; a barrier positioned within the capillary channel to prevent flow of the fluid by capillary action thereacross; and features on opposing sides of the body; and a cartridge having a sample manipulation device, wherein the cartridge has features that correspond to features on the sample collection device to form an axis of rotation, which is substantially perpendicular to the overall direction of the capillary channel from the first end to the second end about which the sample collection device rotates, and wherein the sample collection device is adapted to rotate about the axis of rotation to bring the first end into position with the sample manipulation device. In a preferred embodiment, the sample manipulation portion is an analytical chamber having an analytical reagent thereon, such as a lateral flow assay device.

Still another aspect of the invention is directed to a method for collecting a fluid sample comprising: providing a working element described above; rotating the sample collection device to position the first end in a direction extending away from the cartridge; bringing the first end into contact with the sample, whereby capillary action draws the sample into the channel and to the barrier; rotating the sample collection device to position the first end into position with the sample manipulation device; and applying air pressure to the air vent to force the sample across the barrier and into contact with the sample manipulation device.

Yet another aspect of the invention is directed to a method of performing an assay on a liquid sample for the presence or concentration of one or more analyte(s) or control(s), on the assay device described above, comprising: rotating the sample collection device to position the first end in a direction extending away from the cartridge; bringing the first end into contact with the sample, whereby capillary action draws the sample into the channel and to the barrier; rotating the sample collection device to position the first end into position with assay device; applying air pressure to the air vent to force the sample across the barrier and into contact with a sample addition zone of the assay device; moving the sample by capillary action through a fluid flow path into a reagent zone where it dissolves one or more reagents; flowing the sample away from the reagent zone having a dissolved reagent plume containing one or more reagents and into detection zone(s) by capillary action through the fluid flow path, wherein signal(s) representative of the presence or concentration of analyte(s) or control(s) is produced; and reading the signal(s) that are produced in the detection zones to determine the presence or concentration of the analytes or controls.

Further objects, features and advantages of the present invention will be apparent to those skilled in the art from detailed consideration of the preferred embodiments that follow.

BRIEF DESCRIPTION OF THE DRAWINGS

FIG. 2A shows a perspective view of the working element including the sample collection device in sample collection position according to one embodiment of the invention.

FIG. 2B shows a perspective view of the working element including the sample collection device in sample dispense position according to one embodiment of the invention.

DETAILED DESCRIPTION OF PREFERRED EMBODIMENTS

As used in this specification and the appended claims, the singular forms "a", "an" and "the" include plural referents unless the context clearly dictates otherwise.

The term "about" as used in connection with a numerical value throughout the description and the claims denotes an interval of accuracy, familiar and acceptable to a person skilled in the art. The interval is preferably ±10%.

The term "sample" herein means a volume of a liquid, solution or suspension, intended to be acted upon by a sample manipulation device. In a preferred embodiment, the sample is subjected to qualitative or quantitative determination of any of its properties, such as the presence or absence of a component, the concentration of a component, etc. Typical samples in the context of the present invention are human or animal bodily fluids such as blood, plasma, serum, lymph, urine, saliva, semen, amniotic fluid, gastric fluid, phlegm, sputum, mucus, tears, stool, etc. Other types of samples are derived from human or animal tissue samples where the tissue sample has been processed into a liquid, solution, or suspension to reveal particular tissue components for examination. The embodiments of the present invention are applicable to all bodily samples, but preferably to samples of whole blood, urine or sputum.

In other instances, the sample can be related to food testing, environmental testing, bio-threat or bio-hazard testing, etc. This is only a small example of samples that can be used in the present invention.

Non-biological samples can be aqueous or non-aqueous, for example waste water samples for environmental testing and solutions having organic solvents, such as alcohols for chemical processing. One aspect of the invention is directed to a sample collection device for collecting a sample, such as a blood or blood-based sample, and delivering it to a sample manipulation device that overcomes at least some of the disadvantages of known sample collection devices.

Figure 1:
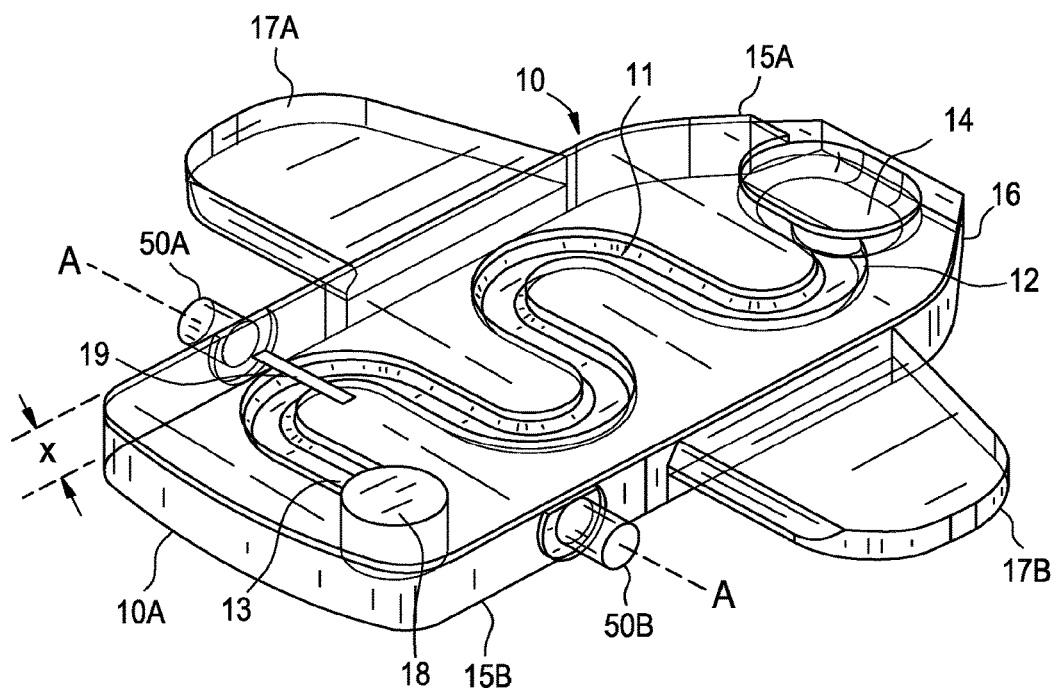
FIG. 1 shows a perspective view of a sample collection device according to one embodiment of the invention.

FIG. 1 shows a preferred embodiment of the sample collection device 10. The device includes a body 10A having a preferably substantially rectangular shaped as shown in FIG. 2A having a thickness "x". The body may be rounded or beveled at its edges as shown by reference number 16. In a particularly preferred embodiment the device may have wings or tabs 17A and 17B (see FIG. 1) extending from the sides of the device to aid in rotating or flipping the device as described below. While the body of the device is preferably rectangular shaped, any shape can be used as long as it has dimensions capable of holding a sufficient amount of sample and can be rotated or flipped. The sample collection device can be made from any suitable material, such as a plastics material, such as polymethyl methacrylate (other plastic materials can include polystyrene, polyethylene, cyclic olefins, acrylics, or moldable polyesters), and is preferably formed by molding such as injection molding. Other possible materials include glass, metal ceramic, etc. The tabs 17A and 17B can be molded or formed together with the body 10A to form one unitary piece. Alternatively, the tabs can be separately applied, such as by adhesive. In a preferred embodiment, the device is at least partially transparent such that the flow of the fluid in the capillary channel can be observed.

Positioned within the body is a capillary channel 11 having dimensions sufficient to hold a desired amount of sample. The capillary channel may have any cross-sectional shape, for example circular or substantially semi-circular ("U" shaped) cross-sections. A substantially semi-circular cross-sectional shape is particularly convenient if the channel is to be defined between two flat components in contact with each other, since only one of the components then needs to be grooved. FIG. 1 shows a particularly preferred embodiment, where the body is made of two flat pieces that are joined together to form the capillary channel. FIG. 1 shows the device with both of the pieces joined. In this embodiment, the top piece 15A is joined to the bottom piece 15B, such as by an adhesive. The top piece is preferably a hydrophilic tape. The dimensions of the channel are selected such that capillary flow of the fluid being sampled will be achieved. For a biological sample, such as blood or plasma, the channel will preferably have a cross-section that is in the range of 0.25-3.0 $mm^2$, preferably 0.5-3.0 $mm^2$. The volume of the capillary channel may be in the range 10 μL to 100 μL, preferably in the range 10 μL to 70 μL, and more preferably 20 μL to 50 μL. The length of the capillary channel is preferably 20 mm-100 mm. For aqueous samples, the capillary channel is preferably treated to render the surface hydrophilic, if it is not already. In addition, for biological samples, such as whole blood, other additives can be included to preserve the biological sample, such as anticoagulants, such as heparin, sodium citrate, or EDTA.

Figure 3A:
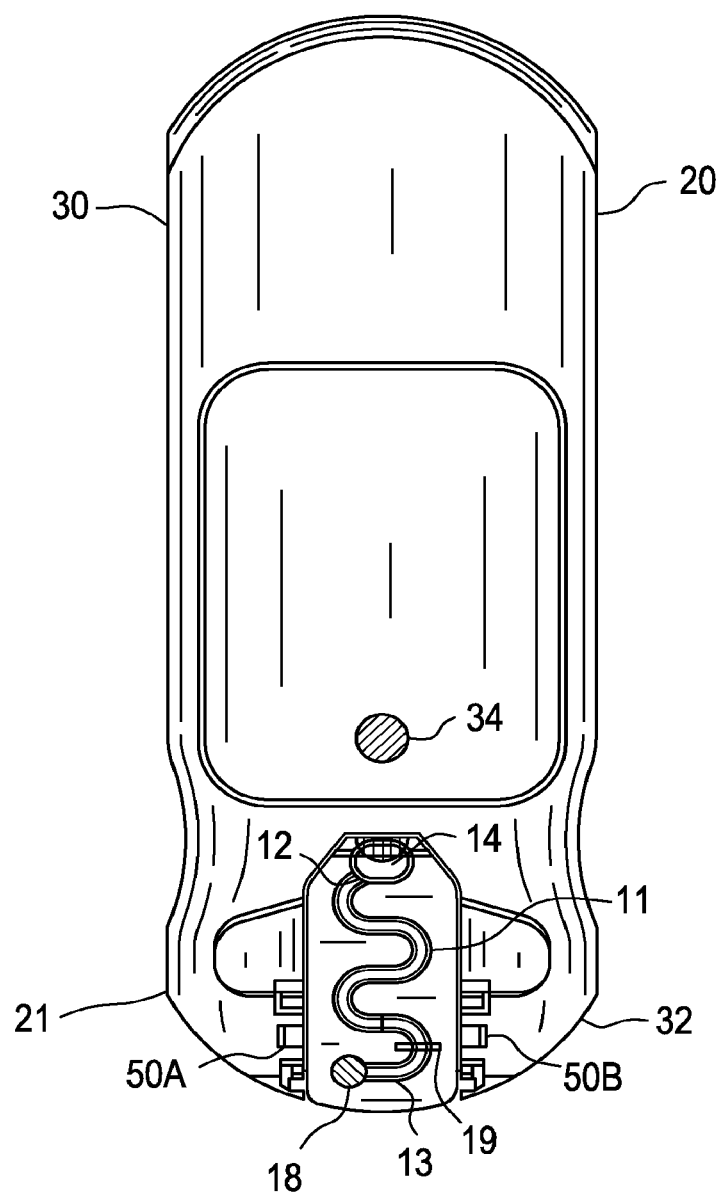
FIG. 3A shows a top planar view of the working element including the sample collection device in sample dispense position according to one embodiment of the invention.
Figure 3B:
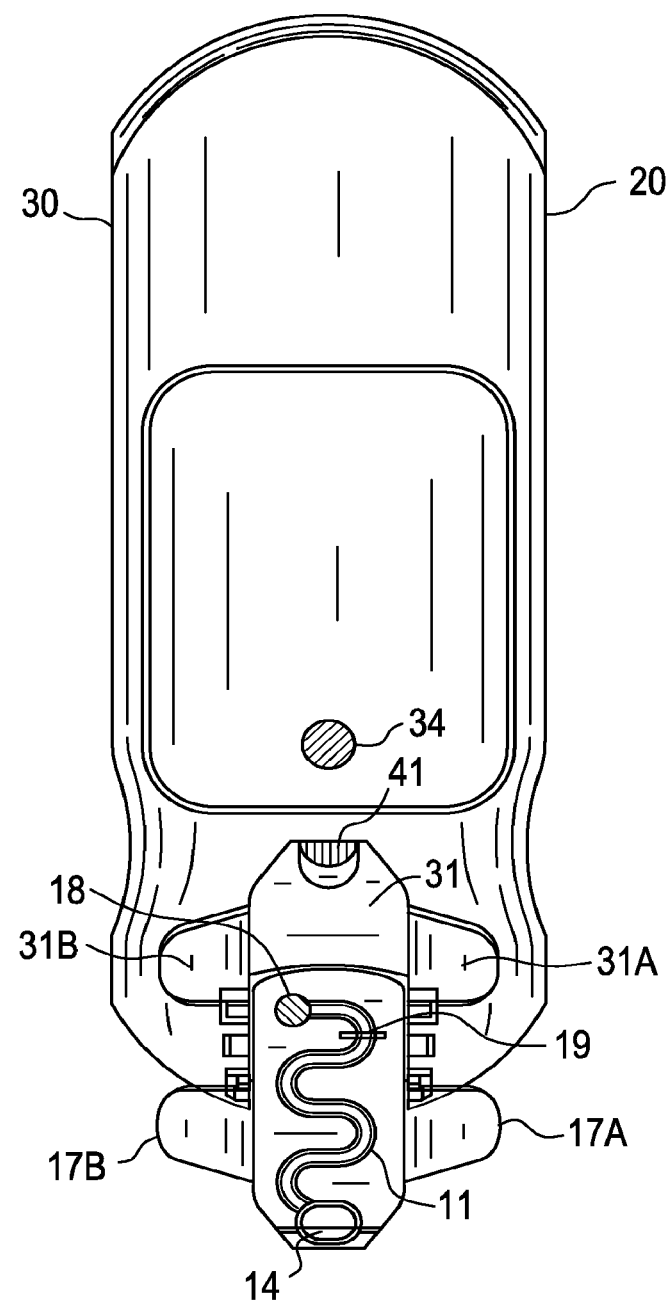
FIG. 3B shows a top planar view of the working element including the sample collection device in sample collection position according to one embodiment of the invention.

The capillary channel has a first end 12 and a second end 13. The first end 12 of the channel is adapted to draw fluid into the capillary channel. In one preferred embodiment as shown in FIG. 2A, the first end 12 opens on the side surface of the body 10A in order to simplify sample collection from a live subject as describe in more detail below. In another preferred embodiment as shown in FIGS. 1, 3A and 3B, the first end includes a sample collection well 14. The sample collection well 14 preferably opens onto the top surface of the body and can simply be a concavity in the top of the body. The collection well is preferably hydrophilic to assist in acquiring and retaining the sample. Various hydrophilic coatings and materials can be used to render the well hydrophilic, including the same materials described with respect to the capillary channel. In a preferred embodiment, the well is be sized to hold approximately the same volume as the channel, so as to prevent possible sample overload. The second end 13 includes an air vent 18 that opens to the outside environment. In a preferred embodiment, the air vent is connected to a source of air pressure to pressurize the capillary channel as described in more detail below. Located between the first and second end is a barrier 19 that prevents the flow of fluid across it. This prevents, among other things, the fluid sample from reaching the second end until it is ready for use and possibly leaking. The barrier can be selected from any material or construction that prevents the flow of sample across it, until a source of air pressure is applied. For example, the barrier can be a hydrophobic porous material, geometric features with sharp edges, a hydrophobic surface, or hydrophobic surface coating. The barrier allows air flow across it so that the sample fluid in the capillary can be acted upon by applied air pressure.

The shape of the capillary channel can be straight or more preferably at least partially non-linear. By having at least a non-linear portion the maximum gravitational forces which can act on the collected sample (with the device in any orientation) are reduced, as compared to a sample in a conventional linear capillary tube of comparable type. In a preferred embodiment, the capillary channel has a serpentine shape as shown in FIG. 1A.

The body of the sample collection device includes features to form an axis of rotation A as shown in FIG. 1. The features can be any type of structure that is capable of cooperating with features in the working element cartridge 30 to provide rotation around the axis A. In a preferred embodiment, the features are pins 50A, 50B that extend perpendicularly outward from the sides of the body to form the axis of rotation A. Alternatively, the features can be corresponding protrusions in the shape of slots to form the axis of rotation A.

The sample collection device is preferably part of a working element 20 for performing some aspect of sample manipulation, such as a diagnostic assay, described in more detail below. Other sample manipulation could include microfluidics devices that can be used to obtain a variety of interesting measurements including molecular diffusion coefficients, fluid viscosity, pH, chemical binding coefficients and enzyme reaction kinetics. Other applications for microfluidic devices include capillary electrophoresis, isoelectric focusing, flow cytometry, sample injection of proteins for analysis via mass spectrometry, PCR amplification, DNA analysis, cell manipulation, cell separation, cell patterning and chemical gradient formation.

The working element 20 includes a cartridge 30 for housing various components of the working element. FIG. 2A is a perspective view of the working element 20 and its components. The sample collection device 10 is located at a first end 21 of the test. When in the dispense position, the sample collection device is preferably fully contained within the cartridge 30 as shown in FIGS. 2B and 3A. Alternatively, when in the dispense position, the sample collection device 10 can be held within the cartridge housing such that a portion of the device 10 protrudes from the end 21 of the working element.

Figure 4:
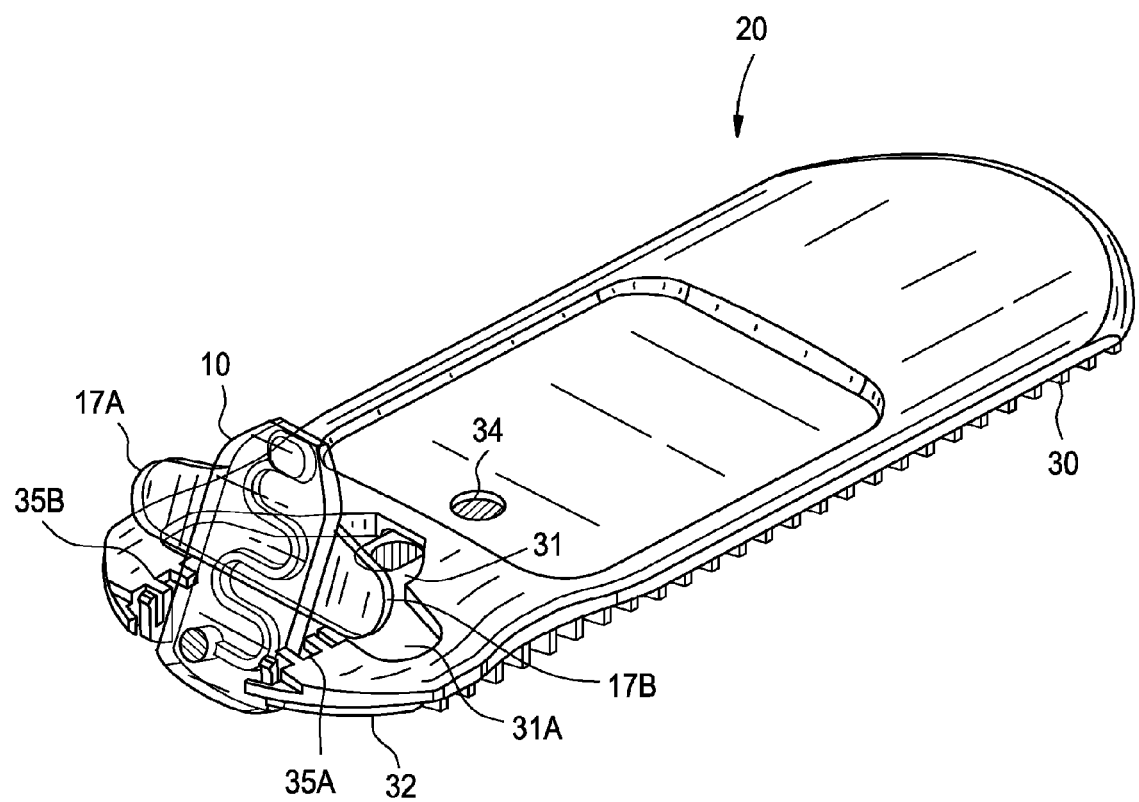
FIG. 4 shows a perspective view of the working element including the sample collection device positioned between a sample collection position and sample dispense position according to one embodiment of the invention.
Figure 5:
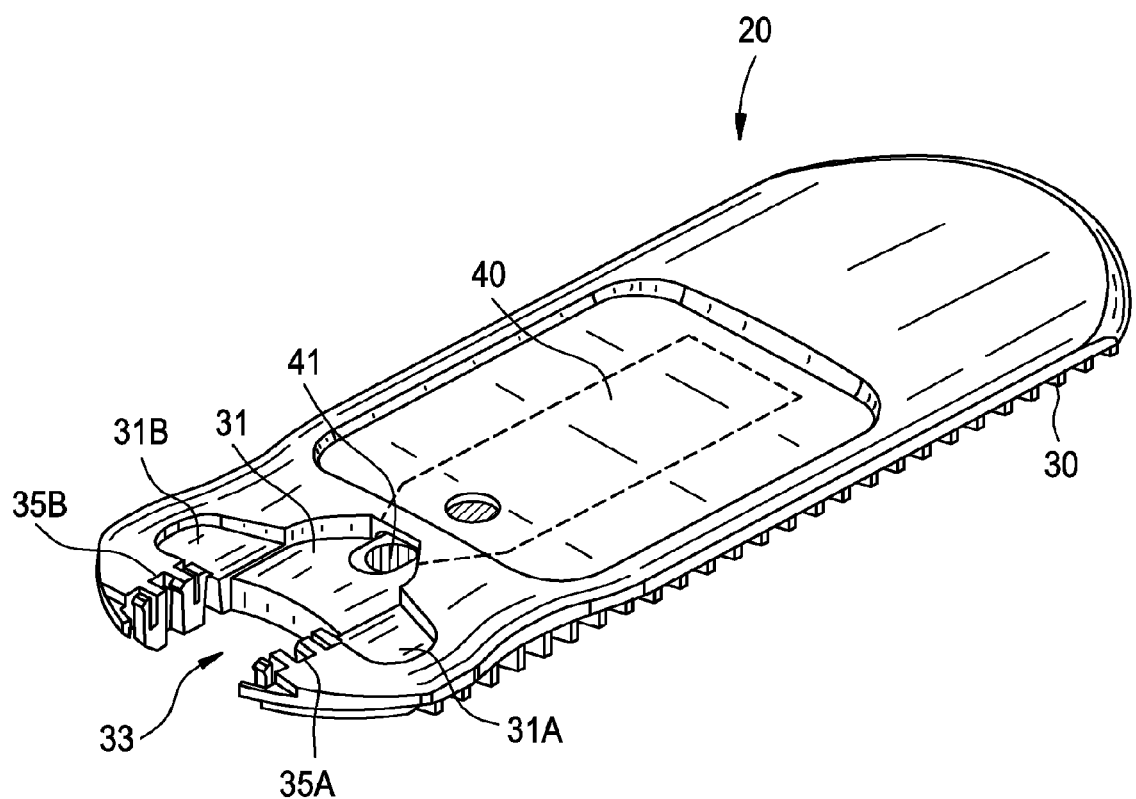
FIG. 5 shows a perspective view of the working element not including the sample collection device according to one embodiment of the invention.

The device 10 sits within a groove or recess 31 that is formed within the cartridge 30 as shown in FIGS. 2A, 3B and 4. The groove 31 preferably conforms to the shape of the collection device 10. If tabs or wings 17A, 17B are include, the groove will have corresponding recesses 31A and 31B, as shown in FIGS. 3B and 4. In a preferred embodiment, the groove terminates before the end of the cartridge housing 32 to form a recess 33 that extends through the entire thickness of the cartridge housing as shown in FIG. 5. This allows for free rotation of the device about axis of rotation A, when the device is in use.

The cartridge housing is preferably formed of two molded halves that can be snap fit together or welded together. Alternatively, the cartridge housing can include molded top cover and a laminated film.

As mentioned above, the cartridge housing includes features that cooperate with the features on the body of the sample collection device to form the axis of rotation A. In a preferred embodiment, the features are slots 35A, 35B as shown in FIG. 5 that cooperate with pins 50 to form the axis of rotation. Alternatively, the cartridge housing can include pins that extend perpendicularly outward from the housing and cooperate with slots in the body of the sample collection device. Any other features that provide an axis of rotation for the sample collection device to rotate around can also be used. In a preferred embodiment, sample collection device is removably held in cartridge. This allows the sample collection device 10 to be provided separately from the rest of the working element 20. This is useful where different types sample collection devices, e.g., with or without well 14, are employed depending on the type of sample to be collected.

Other features of the cartridge housing can include an opening 34 that provides access to the sample manipulation device 40 of the working element. For example, if the sample manipulation device is a lateral flow diagnostic assay the opening 34 can be used to apply a wash fluid to the assay.

The sample collection device 10 is rotatably held within the cartridge housing 30, whereby it can rotate around axis of rotation A between aspirate and dispense positions, or anywhere in-between.

The working element also includes a sample manipulation device 40 for conducting further analysis or processing of a sample. Such processing or analysis can include the microfluidics applications described above. As noted above, a particularly preferred sample manipulation is a lateral flow diagnostic assay described in more detail below with reference to FIGS. 6-8. The sample manipulation device may include a pre-manipulation portion 41, such as a filter for filtering whole blood. After application of the sample to the sample manipulation device 40, the working element can be further used in devices, such as an analyzer for detecting and analyzing a signal, or a chemical processor for further processing of the sample, or any other type of microfluidics devices described above. A particularly preferred analyzer is a fluorometer.

The sample manipulation device 40 and optionally the pre-manipulation portion 41 are in fluid communication with the sample collection device 10 when it is in a dispense position as described below.

As noted above, the sample collection device is rotatable within the cartridge housing. This allows the device to move from a sample collection or aspiration position as shown in FIG. 2A to a dispense position as shown in FIG. 2B where the sample can be dispensed to the sample manipulation device or pre-manipulation portion. In the collection or aspirate position the first end 12 of the capillary channel 11 is exposed to the outside environment, while the second end 13 is within the cartridge housing. In the collection or aspirate position the first end 12 can be directly contacted with the sample to be collected, such as a drop of blood from a finger stick. By capillary forces, the sample will be drawn or aspirated into the capillary channel. Alternatively, the first end can include the sample collection well 14, which can have sample applied to it such as by a syringe filling the sample collection well 14. By capillary forces, the sample will be drawn from the sample well into the capillary channel. Using either embodiment, the progression of the sample into the channel 11 can be observed by a clear top portion 15A.

When a desired amount of sample has been collected, the sample collection device can then be rotated to the dispense position as shown in FIG. 2B and 3A. In the dispense position, the first end 12 of the capillary channel is rotated to position it with the sample manipulation device 40 or pre-manipulation portion 41. A source of compressed air (not shown) is then applied to the second end 13 and the sample is forced to move from the capillary channel through the first end 12 and into the sample manipulation device 40 or pre-manipulation 41 portion of the working element. The compressed air may be supplied by any suitable means, such as by a rubber diaphragm that may or may not be part of an instrument or processing apparatus that further handles the working element.

Another aspect of the invention includes a method for collecting a sample. A working element that includes the components described above is provided. The working element may include the sample collection device already attached from the manufacturer. Alternatively, the sample collection device may be provided separately. This allows the user to select a first end 12 that either includes the sample collection well 14 or not depending on how the sample is to be collected. If the sample collection device is provided separately, the user will have to engage the device with the end of the of cartridge 31. Preferably, slots and pins are provided as described above and the pins will fit in the slots with a snapping engagement. In other words when the pins are inserted into the slots, the pins and/or the slots will deform slightly in order for the larger diameter pins to pass through the top of the slots. When the pins pass through the top of the slots, the pins and/or slots will quickly return to their original shape(s), resulting in a "snapping" sound. One significant advantage to having the sample collection device provided separately is in the event sample is not collected properly, the user would simply use a new sample collection device and would not have to replace the entire working element.

The sample collection device is then rotated into a collection or aspiration position, which is a direction extending away from the cartridge, as shown in FIG. 2A. The first end is then contacted with sample. As discussed above, if the sample to be collected is from a body of an animal, such as a finger stick of blood, the end preferably does not include the sample well 14. If the sample is already in another container, such as a syringe, then it is preferred to dispense the sample into the sample well 14. Capillary action will then draw the sample into the capillary channel 11.

The sample collection device 10 is then rotated about axis of rotation A to bring the first end 12 into a dispense position, where the first end contacts the sample manipulation device 40 or pre-manipulation portion 41, such as a filter. Alternatively, the sample collection device can be held at a position intermediate the collection position and dispense position, such as shown in FIG. 4. This may be useful, where the sample is not ready to be dispensed. After, the sample collection device is rotated to the dispense position, air pressure is applied to the air vent 18 to force sample across the barrier 19 and into contact with the sample manipulation device or pre-manipulation portion.

In a preferred embodiment, the sample manipulation device of the cartridge or a cassette is a diagnostic assay. Diagnostic assays are widespread and central for the diagnosis, treatment and management of many diseases. Different types of diagnostic assays have been developed over the years in order to simplify the detection of various analytes in clinical samples such as blood, serum, plasma, urine, saliva, tissue biopsies, stool, sputum, skin or throat swabs and tissue samples or processed tissue samples. These assays are frequently expected to give a fast and reliable result, while being easy to use and inexpensive to manufacture.

Examples of diagnostic assays include, but are not limited to, the determination of analytes, also called markers, specific for different disorders, e.g. chronic metabolic disorders, such as blood glucose, blood ketones, urine glucose (diabetes), blood cholesterol (atherosclerosis, obesity, etc); markers of other specific diseases, e.g. acute diseases, such as coronary infarct markers (e.g. troponin-T, NT-ProBNP), markers of thyroid function (e.g. determination of thyroid stimulating hormone (TSH)), markers of viral infections (the use of lateral flow immunoassays for the detection of specific viral antibodies); etc.

Yet another important field is the field of companion diagnostics where a therapeutic agent, such as a drug, is administered to an individual in need of such a drug. An appropriate assay is then conducted to determine the level of an appropriate marker to determine whether the drug is having its desired effect. Alternatively, the assay device of the present invention can be used prior to administration of a therapeutic agent to determine if the agent will help the individual in need.

Yet another important field is that of drug tests, for easy and rapid detection of drugs and drug metabolites indicating drug abuse; such as the determination of specific drugs and drug metabolites (e.g. THC) in urine samples etc.

The term "analyte" is used as a synonym of the term "marker" and intended to encompass any chemical or biological substance that is measured quantitatively or qualitatively and can include small molecules, proteins, antibodies, DNA, RNA, nucleic acids, virus components or intact viruses, bacteria components or intact bacteria, cellular components or intact cells and complexes and derivatives thereof.

The term "reaction" is used to define any reaction, which takes place between components of a sample and at least one reagent or reagents on or in the substrate, or between two or more components present in the sample. The term "reaction" is in particular used to define the reaction, taking place between an analyte and a reagent as part of the qualitative or quantitative determination of the analyte.

The term "substrate" means the carrier or matrix to which a sample is added, and on or in which the determination is performed, or where the reaction between analyte and reagent takes place.

A common type of disposable assay device includes a zone or area for receiving the liquid sample, a conjugate zone also known as a reagent zone, and a reaction zone also known as a detection zone. These assay devices are commonly known as lateral flow test strips. They employ a porous material, e.g., nitrocellulose, defining a path for fluid flow capable of supporting capillary flow. Examples include those shown in U.S. Pat. Nos. 5,559,041, 5,714,389, 5,120,643, and 6,228,660 all of which are incorporated herein by reference in their entireties.

The sample-addition zone frequently consists of a more porous material, capable of absorbing the sample, and, when separation of blood cells is desired, also effective to trap the red blood cells. Examples of such materials are fibrous materials, such as paper, fleece, gel or tissue, comprising e.g. cellulose, wool, glass fiber, asbestos, synthetic fibers, polymers, or mixtures of the same.

Another type of assay device is a non-porous assay having projections to induce capillary flow. Examples of such assay devices include the open lateral flow device as disclosed in WO 2003/103835, WO 2005/089082, WO 2005/118139, and WO 2006/137785, all of which are incorporated herein by reference in their entireties.

Figure 6:
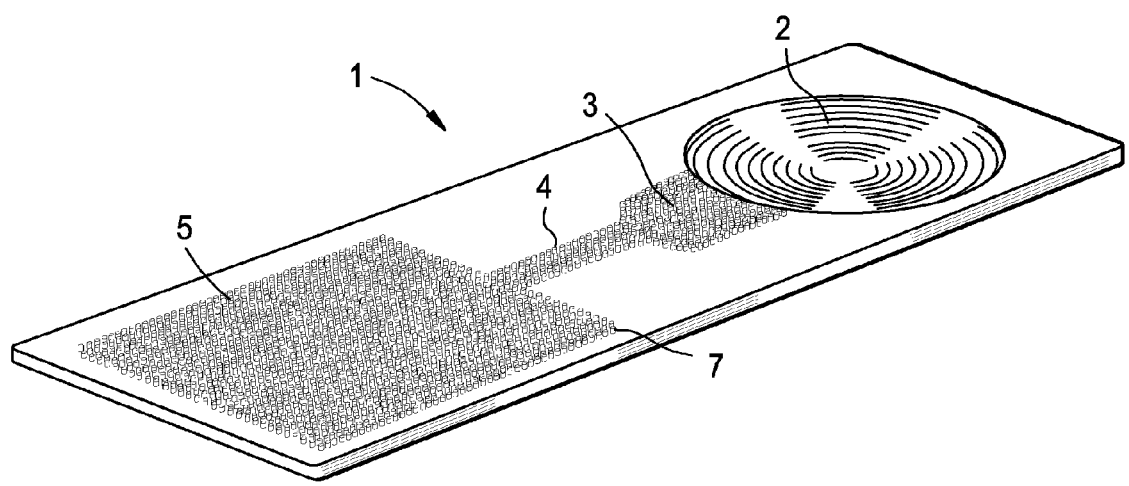
FIG. 6 shows an embodiment of an assay device usable in the present invention.

A non-porous assay device is shown in FIG. 6. The assay device 1, has at least one sample addition zone 2, a reagent zone 3, at least one detection zone 4, and at least one wicking zone 5. The zones form a flow path by which sample flows from the sample addition zone to the wicking zone. Also included are capture elements, such as antibodies, in the detection zone 4, capable of binding to the analyte, optionally deposited on the device (such as by coating); and a labeled conjugate material also capable of participating in reactions that will enable determination of the concentration of the analyte, deposited on the device in the reagent zone, wherein the labeled conjugate material carries a label for detection in the detection zone. The conjugate material is dissolved as the sample flows through the reagent zone forming a conjugate plume of dissolved labeled conjugate material and sample that flows downstream to the detection zone. As the conjugate plume flows into the detection zone, the conjugated material will be captured by the capture elements such as via a complex of conjugated material and analyte (as in a "sandwich" assay) or directly (as in a "competitive" assay. Unbound dissolved conjugate material will be swept past the detection zone into the at least one wicking zone 5.

An instrument such as that disclosed in U.S. 2006/0289787 A1, U.S. 2007/0231883A1, U.S. Pat. No. 7,416,700 and U.S. Pat. No. 6,139,800 all incorporated by reference in their entireties is able to detect the bound conjugated analyte and label in the reaction zone. Common labels include fluorescent dyes that can be detected by instruments which excite the fluorescent dyes and incorporate a detector capable of detecting the fluorescent dyes. Such instruments have a read window that has a width that is typically on the order of 1 mm, which is a generally sufficient width to read enough signal, subject to an adequate width of the conjugate plume.

Figure 7:
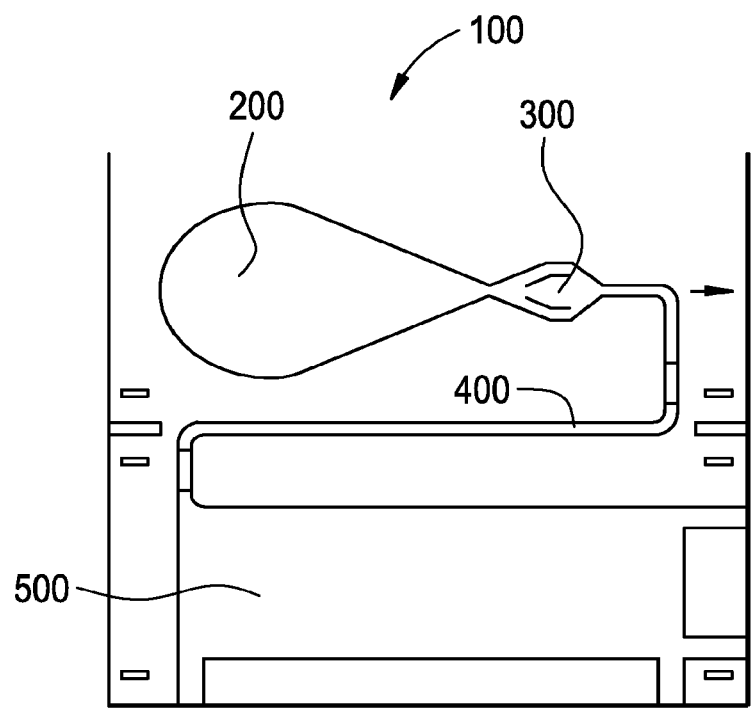
FIG. 7 shows another embodiment of an assay device usable in the present invention.
Figure 8:
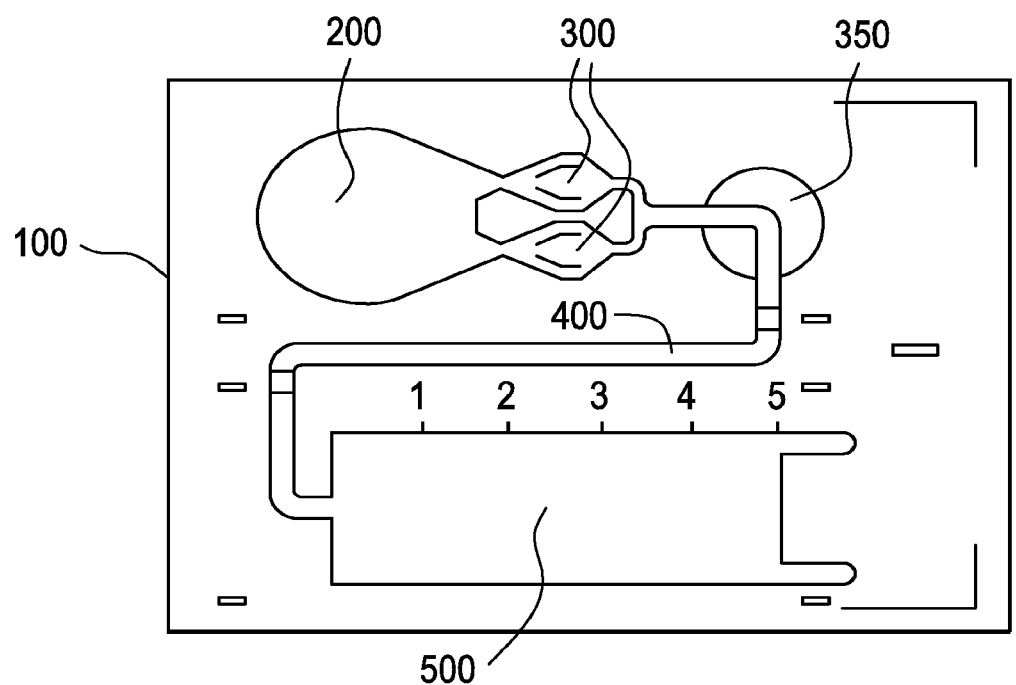
FIG. 8 shows another embodiment of an assay device usable in the present invention.

FIG. 7 shows a schematic view of a preferred lateral flow assay device usable as the sample manipulation device 40. The assay device 100 has at least one sample zone (also referred to as sample addition zone) 200, at least one reagent zone 300, at least one detection zone 400, and at least one wicking zone 500. The zones form a flow path by which sample flows from the sample addition zone to the wicking zone.

Components of the assay device and any other part of the working element (i.e., a physical structure of the device whether or not a discrete piece from other parts of the device) can be prepared from copolymers, blends, laminates, metalized foils, metalized films or metals. Alternatively, device components can be prepared from copolymers, blends, laminates, metalized foils, metalized films or metals deposited one of the following materials: polyolefins, polyesters, styrene containing polymers, polycarbonate, acrylic polymers, chlorine containing polymers, acetal homopolymers and copolymers, cellulosics and their esters, cellulose nitrate, fluorine containing polymers, polyamides, polyimides, polymethylmethacrylates, sulfur containing polymers, polyurethanes, silicon containing polymers, glass, and ceramic materials. Alternatively, components of the device are made with a plastic, elastomer, latex, silicon chip, or metal; the elastomer can comprise polyethylene, polypropylene, polystyrene, polyacrylates, silicon elastomers, or latex. Alternatively, components of the device can be prepared from latex, polystyrene latex or hydrophobic polymers; the hydrophobic polymer can comprise polypropylene, polyethylene, or polyester. Alternatively, components of the device can comprise TEFLON®, polystyrene, polyacrylate, or polycarbonate. Alternatively, device components are made from plastics which are capable of being embossed, milled or injection molded or from surfaces of copper, silver and gold films upon which may be adsorbed various long chain alkanethiols. The structures of plastic which are capable of being milled or injection molded can comprise a polystyrene, a polycarbonate, or a polyacrylate. In a particularly preferred embodiment, the assay device is injection molded from a cyclo olefin polymer, such as those sold under the name Zeonor®. Preferred injection molding techniques are described in U.S. Pat. Nos. 6,372,542, 6,733,682, 6,811,736, 6,884,370, and 6,733,682, all of which are incorporated herein by reference in their entireties.

The flow path can include open or closed paths, grooves, and capillaries. Preferably the flow path comprises a lateral flow path of adjacent projections, having a size, shape and mutual spacing such that capillary flow is sustained through the flow path. In one embodiment, the flow path is in a channel within the substrate having a bottom surface and side walls. In this embodiment, the projections protrude from the bottom surface of the channel. The side walls may or may not contribute to the capillary action of the liquid. If the sidewalls do not contribute to the capillary action of the liquid, then a gap can be provided between the outermost projections and the sidewalls to keep the liquid contained in the flow path defined by the projections. FIG. 6 shows projections 7.

In one embodiment the flow path is at least partially open. In another embodiment the flow path is entirely open. Open means that there is no lid or cover at a capillary distance. Thus the cover, if present as a physical protection for the flow path, does not contribute to the capillary flow in the flow path. An open lateral flow path is described for example in the following published applications: WO 2003/103835; WO 2005/089082; WO 2005/118139; WO 2006/137785; and WO 2007/149042, all of which are incorporated by reference in their entireties. The projections have a height (H), diameter (D) and a distance or distances between the projections (t1, t2) such, that lateral capillary flow of the fluid, such as plasma, preferably human plasma, in the zone is achieved. These dimensions are shown in U.S. 2006/0285996, which is incorporated by reference in its entirety. In addition to optimizing the above-mentioned height, diameter and a distance or distances between the projections, the projections may be given a desired chemical, biological or physical functionality, e.g. by modifying the surface of the projections. In one embodiment, the projections have a height in the interval of about 15 to about 150 µm, preferably about 30 to about 100 µm, a diameter of about 10 to about 160 µm, preferably 40 to about 100 µm, and a gap or gaps between the projections of about 3 to about 200 µm, preferably 5 to about 50 µm or 10 to 50 µm from each other. The flow channel may have a length of about 5 to about 500 mm, preferably about 10 to about 100 mm, and a width of about 0.3 to about 10 mm, preferably about 0.3 to about 3 mm, preferably about 0.5 to 1.5, and preferably about 0.5 to 1.2 mm.

While most detection will occur in the detection zone portion of the fluid flow path, it is also possible that detection may occur in other parts of the device. For example, non-invasive, non-reactive sample integrity measurements may occur between the sample zone and the reagent zone or reagent addition zone, preferably after a filter element, if present. Other measurements may include blanks reads, one part of a two part reaction sequence as for measuring both hemoglobin and glycated hemoglobin for determination of HbA1c, etc.

The liquid sample zone 200, also referred to as the liquid sample addition zone, receives sample from the sample collection device 10. The sample addition zone is capable of transporting the liquid sample from the point where the sample is deposited to the reagent zone, through an optional filter and reagent addition zone, preferably through capillary flow. The capillary flow inducing structure can include porous materials, such as nitrocellulose, or preferably through projections, such as micro-pillars, as shown in FIG. 6. In those devices that can use finger stick volumes of blood, the sample can be directly touched off from the finger, or by a capillary pipette.

Located between the sample addition zone and the detection zone is a reagent zone 300. The reagent zone can include reagent material(s) integrated into the analytical element and are generally reagents useful in the reaction—binding partners such as antibodies or antigens for immunoassays, substrates for enzyme assays, probes for molecular diagnostic assays, or are auxiliary materials such as materials that stabilize the integrated reagents, materials that suppress interfering reactions, etc. Generally one of the reagents useful in the reaction bears a detectable signal as discussed below. In some cases the reagents may react with the analyte directly or through a cascade of reactions to form a detectable signal such as, but not restricted to, a molecule detectable using spectroscopy such as a colored or fluorescent molecule. In one preferred embodiment, the reagent zone includes conjugate material. The term conjugate means any moiety bearing both a detection element and a binding partner.

The detection element is an agent which is detectable with respect to its physical distribution or/and the intensity of the signal it delivers, such as but not limited to luminescent molecules (e.g. fluorescent agents, phosphorescent agents, chemiluminescent agents, bioluminescent agents and the like), colored molecules, molecules producing colors upon reaction, enzymes, radioisotopes, ligands exhibiting specific binding and the like. The detection element also referred to as a label is preferably chosen from chromophores, fluorophores, radioactive labels, and enzymes. Suitable labels are available from commercial suppliers, providing a wide range of dyes for the labeling of antibodies, proteins, and nucleic acids. There are, for example, fluorophores spanning practically the entire visible and infrared spectrum. Suitable fluorescent or phosphorescent labels include for instance, but are not limited to, fluoresceins, Cy3, Cy5 and the like. Suitable chemoluminescent labels are for instance but are not limited to luminol, cyalume and the like.

Similarly, radioactive labels are commercially available, or detection elements can be synthesized so that they incorporate a radioactive label. Suitable radioactive labels are for instance but are not limited to radioactive iodine and phosphorus; e.g. $^{125}$I and $^{32}$P.

Suitable enzymatic labels are, for instance, but are not limited to, horseradish peroxidase, beta-galactosidase, luciferase, alkaline phosphatase and the like. Two labels are "distinguishable" when they can be individually detected and preferably quantified simultaneously, without significantly disturbing, interfering or quenching each other. Two or more labels may be used, for example, when multiple analytes or markers are being detected.

The binding partner is a material that can form a complex that can be used to determine the presence of or amount of an analyte. For example, in an "sandwich" assay, the binding partner in the conjugate can form a complex including the analyte and the conjugate and that complex can further bind to another binding partner, also called a capture element, integrated into the detection zone. In a competitive immunoassay, the analyte will interfere with binding of the binding partner in the conjugate to another binding partner, also called a capture element, integrated into the detection zone. Example binding partners included in conjugates include antibodies, antigens, analyte or analyte-mimics, protein, etc.

Optionally located in the fluid flow path, before or after the reagent zone and before the detection zone is a reagent addition zone. The reagent addition zone is shown as 350 in FIG. 8. The reagent addition zone can allow addition of a reagent externally from the device. For example, the reagent addition zone may be used to add an interrupting reagent that may be used to wash the sample and other unbound components present in the fluid flow path into the wicking zone. In a preferred embodiment the reagent addition zone 350 is located after the reagent zone 300.

Downstream from the liquid sample zone and the reagent zone is the detection zone 400 which is in fluid communication with the sample addition zone. The detection zone 400 may include projections such as those described above. As also noted above, these projections are preferably integrally molded into the substrate from an optical plastic material such as Zeonor, such as injection molding or embossing. The width of the flow channel in the detection zone is typically on the order of 2 mm for conventional size devices, however, some lower volume devices, such as those described above and in co pending application entitled "Lower Volume Assay Device Having Increased Sensitivity," Ser. No. 13/744,617, filed on Jan. 20, 2013, (now U.S. Patent Application Publication No. 2014/0206098 A1) and incorporated by reference in its entirety, are significantly narrower, e.g., 1.5 mm or less, preferably 0.5 to 1.2 mm.

The detection zone is where any detectable signal is read. In a preferred embodiment attached to the projections in the detection zone are capture elements. The capture elements can include binding partners for the conjugate or complexes containing the conjugate, as described above. For example, if the analyte is a specific protein, the conjugate may be an antibody that will specifically bind that protein coupled to a detection element such as a fluorescence probe. The capture element could then be another antibody that also specifically binds to that protein. In another example, if the marker or analyte is DNA, the capture molecule can be, but is not limited to, synthetic oligonucleotides, analogues thereof, or specific antibodies. Other suitable capture elements include antibodies, antibody fragments, aptamers, and nucleic acid sequences, specific for the analyte to be detected. A non-limiting example of a suitable capture element is a molecule that bears avidin functionality that would bind to a conjugate containing a biotin functionality. The detection zone can include multiple detection zones. The multiple detection zones can be used for assays that include one or more markers. In the event of multiple detection zones, the capture elements can include multiple capture elements, such as first and second capture elements. The conjugate can be pre-deposited on the assay device, such as by coating in the reagent zone. Similarly the capture elements can be pre-deposited on the assay device on the detection zone. Preferably, both the detection and capture elements are pre-deposited on the assay device, on the detection zone and detection zone, respectively.

After the sample has been delivered to the sample zone, it will encounter the reagent zone. After the sample has flowed through and interacted with the reagent zone and optionally the reagent addition zone, the sample and a reagent plume will be contained in the fluid flow. The reagent plume can contain any of the reagent materials that have been dissolved in the detection zone or those added through the reagent addition zone. The reagent in the sample flowing from the reagent zone, but before the reagent addition zone is considered to be a reagent plume. The reagent plume can include the conjugate having both the detection element and binding partner, in which case it is often referred to as a conjugate plume.

Downstream from the detection zone is a wicking zone in fluid communication with the detection zone. The wicking zone is an area of the assay device with the capacity of receiving liquid sample and any other material in the flow path, e.g., unbound reagents, wash fluids, etc. The wicking zone provides a capillary force to continue moving the liquid sample through and out of the detection zone. The wicking zone can include a porous material such as nitrocellulose or can be a non-porous structure such as the projections described herein. The wicking zone can also include non-capillary fluid driving means, such as using evaporative heating or a pump. Further details of wicking zones as used in assay devices according to the present invention can be found in patent publications U.S. 2005/0042766 and U.S. 2006/0239859, both of which are incorporated herein by reference in their entireties. Wicking zones are also described in patent application entitled "Controlling Fluid Flow Through An Assay Device," Ser. No. 13/744,641, filed on Jan. 18, 2013, (now U.S. Patent Application Publication No. 2013/0210036 A1) and incorporated by reference in its entirety.

Preferably the entirety of the flow path including the sample addition zone, the detection zone and the wicking zone includes projections substantially vertical in relation to the substrate, and having a height, diameter and reciprocal spacing capable of creating lateral flow of the sample in the flow path.

In any of the above embodiments, the device is preferably a disposable assay device. The assay device may be contained in a housing for ease of handling and protection. If the assay device is contained in such a housing, the housing will preferably include a port for adding sample to the assay device.

The assay device of the present invention can be used with a device for reading (a reader) the result of an assay device performed on the assay of the present invention. The reader includes means for reading a signal emitted by, or reflected from the detection element, such as a photodetector, and means for computing the signal and displaying a result, such as microprocessor that may be included within an integrated reader or on a separate computer. Suitable readers are described for example in U.S. 2007/0231883 and U.S. Pat. No. 7,416,700, both of which are incorporated by reference in their entireties.

Another embodiment is a device for reading the result of an assay performed on an assay device, wherein the device comprises a detector capable of reading a signal emitted from or reflected from at least one detection element present in a defined location of the assay device. In either of the above embodiments, the reading preferably is chosen from the detection and/or quantification of color, fluorescence, radioactivity or enzymatic activity.

The assay device along with the rest of the cartridge can be used to perform an assay on a liquid sample for the detection of one or more analytes of interest. A liquid sample containing the analyte(s) of interest is collected using the sample collection device as described above and is then dispensed onto the sample zone of the assay device. The sample moves by capillary action through an optional filter and into the reagent zone where it encounters the multiple reagent materials. The sample flows past the first, second and third reagent material. The reagent material flowing past the second and third reagent materials form second and third reagent plumes along the edges of the reagent cell. The sample flowing past the first reagent material forms a first reagent plume long the line of symmetry of the reagent cell. The first, second and third reagent material combine upon leaving the reagent cell to form a combined reagent plume.

Next the sample and reagent plume move by capillary action into the detection zone. There a signal representative of the presence or concentration of the analyte(s) or control is produced. In a preferred embodiment the sample or the one or more reagents having a detection element is captured having in the detection zone, such as by antibodies on the surface of the detection zone and a signal representative of the presence or concentration of the analyte(s) or control(s) is produced.

The reader as described above is then used to read the signal that is produced by the detection element to determine the presence or concentration of the analyte(s). The sample moves from the detection zone and into the wicking zone. The reader may read the signal immediately or a short time after the sample has moved through the detection zone. Also, one or more washes may follow the sample through the device to wash any unbound detection element away from the detection zone. The cartridge 20 containing the lateral flow assay device can be inserted into the reader either before or after the sample has been dispensed to the sample zone. In those embodiments where a source of compressed air is used to dispense the sample, the cartridge can first be inserted into the reader and the compressed air can then be used to force sample from the sample collection device to the assay device.

The method, assay device, and reader according to an embodiment of the invention have many advantages, mainly related to the improved detection kinetics of the immunochemical reactions and the increased sensitivity of the assay. It is to be understood that this invention is not limited to the particular embodiments shown here.

Additional Embodiments

1. A sample collection device for a fluid sample, the device comprising: a body including a capillary channel having a first end and a second end, wherein the first end is adapted to draw the fluid into the channel by capillary action; an air vent located in the vicinity of the second end and in fluid communication with the capillary channel; a barrier positioned within the capillary channel to prevent flow of the fluid by capillary action there across; and features on opposing sides of the body to form an axis of rotation, which is substantially perpendicular to the overall direction of the capillary channel from the first end to the second end.

2. A sample collection device as disclosed in embodiment 1, wherein the sample collection device is adapted to rotate about the axis of rotation within a cartridge having a sample manipulation device to bring the first end into position with the sample manipulation device.

3. A sample collection device as disclosed in embodiment 1, wherein at least a portion of the capillary channel is non-linear.

4. A sample collection device as disclosed in embodiment 1, wherein the barrier comprises a portion of the surface of the channel that is hydrophobic.

5. A sample collection device as disclosed in embodiment 1, wherein first end of the channel is hydrophilic.

6. A sample collection device as disclosed in embodiment 5, wherein the first end is provided with a hydrophilic coating.

7. A sample collection device as disclosed in embodiment 1, wherein the body has a substantially rectangular shape, and wherein the first end is located at the first shorter dimension and the second end is located in the vicinity of the second shorter dimension.

8. A sample collection device as disclosed in embodiment 7, wherein the features on opposing sides of the body are located on the longer dimensions.

9. A sample collection device as disclosed in embodiment 8, wherein the features are projections extending outwardly from the body.

10. A sample collection device as disclosed in embodiment 1, wherein the barrier is selected from the group consisting of a hydrophobic porous material, geometric features with sharp edges, a hydrophobic surface, or hydrophobic surface coating, whereby the barrier allows air flow to the capillary channel so that the sample in the capillary can be acted upon by applied air pressure.

11. A working element comprising: a sample collection device for a sample fluid, the device comprising: a body including a capillary channel having a first end and a second end, wherein the first end is adapted to draw the fluid into the channel by capillary action; an air vent located in the vicinity of the second end and in fluid communication with the capillary channel; a barrier positioned within the capillary channel to prevent flow of the fluid by capillary action thereacross; and features on opposing sides of the body; and a cartridge having a sample manipulation device, wherein the cartridge has features that correspond to features on the sample collection device to form an axis of rotation, which is substantially perpendicular to the overall direction of the capillary channel from the first end to the second end about which the sample collection device rotates, and wherein the sample collection device is adapted to rotate about the axis of rotation to bring the first end into position with the sample manipulation device.

12. A working element as disclosed in embodiment 11, wherein the sample manipulation device includes at least one filter in fluid communication with the first end of the capillary channel.

13. A working element as disclosed in embodiment 11, wherein the sample manipulation device is an analytical chamber in fluid communication with the first end of the capillary channel.

14. A working element as disclosed in embodiment 13, wherein the analytical chamber is provided with an analytical reagent thereon.

15. A working element as disclosed in embodiment 14, wherein the analytical chamber is a lateral flow assay device.

16. A working element as disclosed in embodiment 11, wherein the body has a substantially rectangular shape, and wherein the first end is located at the first shorter dimension and the second end is located in the vicinity of the second shorter dimension.

17. A working element as disclosed in embodiment 11, wherein the sample collection device is located at a first end of the cartridge housing.

18. A working element as disclosed in embodiment 17, wherein a portion of the cartridge has a groove which at least partially contains the sample collection device.

19. A working element as disclosed in embodiment 17, wherein the body has a substantially rectangular shape, and wherein the first end is located at the first shorter dimension and the second end is located in the vicinity of the second shorter dimension.

20. A working element as disclosed in embodiment 19, wherein the features of the cartridge that form the axis of rotation are located in the portion of the housing that forms the groove or a recess within the groove, whereby the sample collection device rotates from a position where the first end extends away from the cartridge to a position where the first end is in contact with the sample manipulation device.

21. A working element as disclosed in embodiment 18, the features of the sample collection device comprise pins and the features of the cartridge housing comprise slots which cooperate with the pins to form the axis of rotation.

22. A method for collecting a fluid sample comprising: providing a working element which comprises: a sample collection device for a fluid sample, the device comprising: a body including a capillary channel having a first end and a second end, wherein the first end is adapted to draw the fluid into the channel by capillary action; an air vent located in the vicinity of the second end and in fluid communication with the capillary channel; a barrier positioned within the capillary channel to prevent flow of the fluid by capillary action thereacross; and features on opposing sides of the body; and a cartridge having a sample manipulation device, wherein the cartridge has features that correspond to features on the sample collection device to form an axis of rotation, which is substantially perpendicular to the overall direction of the capillary channel from the first end to the second end about which the sample collection device rotates, and wherein the sample collection device is adapted to rotate about the axis of rotation to bring the first end into position with the sample manipulation device; rotating the sample collection device to position the first end in a direction extending away from the cartridge; bringing the first end into contact with the sample, whereby capillary action draws the sample into the channel and to the barrier; rotating the sample collection device to position the first end into position with the sample manipulation device; and applying air pressure to the air vent to force the sample across the barrier and into contact with the sample manipulation device.

23. A method as disclosed in embodiment 22, wherein the sample is an aqueous fluid sample.

24. A sample collection device as disclosed in embodiment 23, wherein the fluid is a bodily fluid.

25. A method of as disclosed in embodiment 23, wherein the sample is whole blood, serum, plasma or urine.

26. A method as disclosed in embodiment 22, wherein the step of bringing the first end into contact with the sample comprises bringing the first end into contact with a drop of blood on an animal.

27. A method as disclosed in embodiment 26, wherein the animal is a mammal.

28. A method as disclosed in embodiment 27, wherein the mammal is a human.

29. A method as disclosed in embodiment 22, wherein the step of bringing the first end into contact with the sample comprises bringing the first end into contact with a syringe containing blood from an animal.

30. A method as disclosed in embodiment 22, wherein the sample manipulation device includes a sample pre-manipulation portion comprising at least one filter in fluid communication with the first end of the capillary channel.

31. A method as disclosed in embodiment 22, wherein the sample manipulation device is an analytical chamber in fluid communication with the first end of the capillary channel.

32. A method as disclosed in embodiment 31, wherein the analytical chamber is provided with an analytical reagent.

33. A method as disclosed in embodiment 22, wherein the body has a substantially rectangular shape, and wherein the first end is located at the first shorter dimension and the second end is located in the vicinity of the second shorter dimension.

34. A method as disclosed in embodiment 22, wherein the sample collection device is located at a first end of the cartridge housing.

35. A method as disclosed in embodiment 34, wherein a portion of the cartridge housing has a groove which contains the sample collection device.

36. A method as disclosed in embodiment 35, wherein the body has a substantially rectangular shape, and wherein the first end is located at the first shorter dimension and the second end is located in the vicinity of the second shorter dimension.

37. A method as disclosed in embodiment 36, wherein the features of the cartridge that form the axis of rotation are located in the portion of the housing that forms the groove or a recess in the groove, whereby the sample collection device rotates from a position where the first end extends away from the cartridge to a position where the first end is in contact with the sample manipulation device.

38. A method of performing an assay on a liquid sample for the presence or concentration of one or more analyte(s) or control(s), on the assay device according to embodiment 15, comprising: rotating the sample collection device to position the first end in a direction extending away from the cartridge; bringing the first end into contact with the sample, whereby capillary action draws the sample into the channel and to the barrier; rotating the sample collection device to position the first end into position with assay device; applying air pressure to the air vent to force the sample across the barrier and into contact with a sample addition zone of the assay device; moving the sample by capillary action through a fluid flow path into a reagent zone where it dissolves one or more reagents; flowing the sample away from the reagent zone having a dissolved reagent plume containing one or more reagents and into detection zone(s) by capillary action through the fluid flow path, wherein signal(s) representative of the presence or concentration of analyte(s) or control(s) is produced; and reading the signal(s) that are produced in the detection zones to determine the presence or concentration of the analytes or controls.

Those skilled in the art will appreciate that the invention and embodiments thereof described herein are susceptible to variations and modifications other than those specifically described. It is to be understood that the invention includes all such variations and modifications. The invention also includes all of the steps and features referred to in this specification, individually or collectively, and any and all combinations of any two or more of the steps or features.

The invention claimed is:

1. A sample collection device for a fluid sample, the device comprising:
   a body including a capillary channel having a first end and a second end, wherein the first end is adapted to draw the fluid into the channel by capillary action;
   an air vent located in the vicinity of the second end and in fluid communication with the capillary channel;
   a barrier positioned within the capillary channel to prevent flow of the fluid by capillary action thereacross; and
   features on opposing sides of the body to form an axis of rotation, which is substantially perpendicular to the overall direction of the capillary channel from the first end to the second end.

2. A sample collection device as claimed in claim 1, wherein the sample collection device is adapted to rotate about the axis of rotation within a cartridge having a sample manipulation device to bring the first end into position with the sample manipulation device.

3. A sample collection device as claimed in claim 1, wherein at least a portion of the capillary channel is non-linear.

4. A sample collection device as claimed in claim 1, wherein the barrier comprises a portion of the surface of the capillary channel that is hydrophobic.

5. A sample collection device as claimed in claim 1, wherein the first end of the capillary channel is hydrophilic.

6. A sample collection device as claimed in claim 5, wherein the first end is provided with a hydrophilic coating.

7. A sample collection device as claimed in claim 1, wherein the body has a substantially rectangular shape, and wherein the first end is located at a first shorter dimension of the shape and the second end is located in the vicinity of a second shorter dimension of the shape.

8. A sample collection device as claimed in claim 7, wherein the features on opposing sides of the body are located on the longer dimensions of the substantially rectangular shape.

9. A sample collection device as claimed in claim 8, wherein the features are projections extending outwardly from the body.

10. A sample collection device as claimed in claim 1, wherein the barrier is selected from the group consisting of a hydrophobic porous material, geometric features with sharp edges, a hydrophobic surface, or hydrophobic surface coating, whereby the barrier allows air flow to the capillary channel so that the sample in the capillary can be acted upon by applied air pressure.

11. A working element comprising:
a sample collection device as recited in claim 1; and
a cartridge having a sample manipulation device, wherein the cartridge has features that correspond to the features on the sample collection device to form the axis of rotation about which the sample collection device rotates, and wherein the sample collection device is adapted to rotate about the axis of rotation to bring the first end into position with the sample manipulation device.

12. A working element as claimed in claim 11, wherein the sample manipulation device includes at least one filter in fluid communication with the first end of the capillary channel.

13. A working element as claimed in claim 11, wherein the sample manipulation device is an analytical chamber in fluid communication with the first end of the capillary channel.

14. A working element as claimed in claim 13, wherein the analytical chamber is provided with an analytical reagent thereon.

15. A working element as claimed in claim 14, wherein the analytical chamber is a lateral flow assay device.

16. A working element as claimed in claim 11, wherein the sample collection device is located at a first end of a cartridge housing.

17. A working element as claimed in claim 16, wherein a portion of the cartridge has a groove which at least partially contains the sample collection device.

18. A working element as claimed in claim 17, wherein the features of the cartridge that form the axis of rotation are located in the portion of the housing that forms the groove or a recess within the groove, whereby the sample collection device rotates from a position where the first end extends away from the cartridge to a position where the first end is in contact with the sample manipulation device.

19. A working element as claimed in claim 17, wherein the features of the sample collection device comprise pins and the features of the cartridge housing comprise slots which cooperate with the pins to form the axis of rotation.

20. A method of performing an assay on a liquid sample for the presence or concentration of one or more analyte(s) or control(s), on the assay device according to claim 15, comprising:
rotating the sample collection device to position the first end in a direction extending away from the cartridge;
bringing the first end into contact with the sample, whereby capillary action draws the sample into the channel and to the barrier;
rotating the sample collection device to position the first end into position with the assay device;
applying air pressure to the air vent to force the sample across the barrier and into contact with a sample addition zone of the assay device;
moving the sample by capillary action through a fluid flow path into a reagent zone where it dissolves one or more reagents;
flowing the sample away from the reagent zone having a dissolved reagent plume containing one or more reagents and into detection zone(s) by capillary action through the fluid flow path, wherein signal(s) representative of the presence or concentration of analyte(s) or control(s) is produced; and
reading the signal(s) that are produced in the detection zones to determine the presence or concentration of the analytes or controls.

* * * * *